United States Patent
Igarashi

(10) Patent No.: US 10,330,636 B2
(45) Date of Patent: Jun. 25, 2019

(54) GAS SENSOR ELEMENT, GAS SENSOR, AND METHOD OF MANUFACTURING GAS SENSOR ELEMENT

(71) Applicant: NGK SPARK PLUG CO., LTD., Nagoya-shi, Aichi (JP)

(72) Inventor: Ai Igarashi, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 458 days.

(21) Appl. No.: 15/139,899

(22) Filed: Apr. 27, 2016

(65) Prior Publication Data

US 2016/0320333 A1    Nov. 3, 2016

(30) Foreign Application Priority Data

Apr. 30, 2015  (JP) .................................. 2015-092548

(51) Int. Cl.
  *G01N 27/407* (2006.01)
  *G01N 27/409* (2006.01)
(52) U.S. Cl.
  CPC ........ *G01N 27/409* (2013.01); *G01N 27/4071* (2013.01)
(58) Field of Classification Search
  CPC ............... G01N 27/407; G01N 27/409; G01N 27/4071; G01N 27/406–41; G01N 33/0004–0075
  See application file for complete search history.

(56) References Cited

U.S. PATENT DOCUMENTS

| | | | | |
|---|---|---|---|---|
| 4,145,272 A | * | 3/1979 | Nakamura | ........... G01N 27/407 204/412 |
| 5,144,249 A | * | 9/1992 | Kurishita | ........... G01N 27/4071 204/426 |

(Continued)

FOREIGN PATENT DOCUMENTS

JP    2010-145214 A    7/2010

OTHER PUBLICATIONS

Bica et al. (AM Bica, Optimization at the end-points the Akima's interpolation method of smooth curve fitting, Computer Aided Geometric Design 31 (2014) 245-257) (Year: 2014).*

(Continued)

*Primary Examiner* — Maris R Kessel
*Assistant Examiner* — Joshua L Allen
(74) *Attorney, Agent, or Firm* — Sughrue Mion, PLLC

(57) ABSTRACT

A gas sensor element including a composite ceramic layer including a plate-shaped insulating portion containing an insulating ceramic and having a through hole formed therein and a plate-shaped electrolyte portion containing a solid electrolyte ceramic and disposed in the through hole; and a first conductor layer extending continuously from a first insulating surface on one side of the insulating portion to a first electrolyte surface of the electrolyte portion facing the same direction as the one side of the insulating portion. The first insulating surface is flush with the first electrolyte surface. The electrolyte portion has, on its first electrolyte surface side, an extension portion extending outward from the through hole so as to overlap the first insulating surface. Further, the thickness of the extension portion decreases toward the outer circumference of the extension portion. Also disclosed is a method of manufacturing the gas sensor element.

3 Claims, 9 Drawing Sheets

(56) References Cited

U.S. PATENT DOCUMENTS

| | | | | |
|---|---|---|---|---|
| 5,384,030 | A * | 1/1995 | Duce | G01N 27/4073 |
| | | | | 204/400 |
| 5,431,806 | A * | 7/1995 | Suzuki | G01N 27/404 |
| | | | | 204/403.06 |
| 6,327,891 | B1 * | 12/2001 | Noda | G01N 27/407 |
| | | | | 204/424 |
| 6,645,360 | B1 * | 11/2003 | Eisele | G01N 27/4077 |
| | | | | 204/408 |
| 2005/0189222 | A1 * | 9/2005 | Tsuzuki | B28B 1/008 |
| | | | | 204/424 |
| 2011/0198674 | A1 * | 8/2011 | Krauss | G01N 27/4141 |
| | | | | 257/253 |
| 2013/0032480 | A1 * | 2/2013 | Ito | G01N 27/406 |
| | | | | 204/424 |

OTHER PUBLICATIONS

MathOnline (MathOnline, http://mathonline.wikidot.com/plane-curves-and-space-curves, accessed Nov. 5, 2018) (Year: 2018).*

* cited by examiner

GAS SENSOR ELEMENT, GAS SENSOR, AND METHOD OF MANUFACTURING GAS SENSOR ELEMENT

BACKGROUND OF THE INVENTION

1. Field of the Invention

The present invention relates to a gas sensor element, to a gas sensor, and to a method of manufacturing a gas sensor element.

2. Description of the Related Art

A gas sensor is used for combustion control for an internal combustion engine. The gas sensor includes a gas sensor element that outputs a detection signal indicative of the concentration of a particular component (e.g., oxygen) of exhaust gas emitted from the internal combustion engine. For example, a gas sensor element described in Patent Document 1 includes alumina sheets each having a through hole extending in a thickness direction, and a zirconia filling portion having oxygen ionic conductivity is embedded in each of the through holes. A pair of electrodes are disposed on opposite surfaces of each zirconia filling portion. Patent Document 1 shows a structure in which the thickness of the zirconia filling portion is made larger than the depth of the through hole (i.e., the thickness of the alumina sheet) such that the zirconia filling portion protrudes from the through hole, and the size of the protruding portion of the zirconia filling portion is made larger than the opening area of the through hole.

[Patent Document 1] Japanese Patent Application Laid-Open (kokai) No. 2010-145214

3. PROBLEMS TO BE SOLVED BY THE INVENTION

Generally, wiring layers (conductor layers) for outputting an electric signal from the electrodes disposed on the zirconia filling portion to the outside of a sensor element are disposed on the alumina sheet. However, in Patent Document 1, there is no disclosure concerning such wiring layers. With the structure of the zirconia filling portion shown in Patent Document 1, when a wiring layer is disposed so as to extend from an electrode on the zirconia filling portion to an edge portion of the alumina sheet, the wiring layer may be cracked or broken at an edge of the zirconia filling portion that is located outside the through hole. Therefore, there is a need for a technique capable of suppressing the occurrence of cracking or breakage of a conductor layer including an electrode and a wiring layer in a gas sensor element including an insulating portion having a through hole and an electrolyte portion embedded in the through hole.

SUMMARY OF THE INVENTION

The present invention has been made to solve the above problem. It is therefore an object of the present invention to suppress the occurrence of cracking or breakage of a conductor in a gas sensor element including an insulating portion having a through hole and an electrolyte portion embedded in the through hole.

The above object has been achieved by providing, in a first aspect (1), a gas sensor element comprising: a composite ceramic layer including a plate-shaped insulating portion that contains an insulating ceramic and has a through hole passing through the insulating portion in a thickness direction thereof and a plate-shaped electrolyte portion that contains a solid electrolyte ceramic and is disposed in the through hole; and a first conductor layer extending continuously from a first insulating surface on one side of the insulating portion to a first electrolyte surface of the electrolyte portion facing the same direction as the one side of the insulating portion. The first insulating surface is flush with the first electrolyte surface, the electrolyte portion has an extension portion located on the side where the first electrolyte surface is present and extending outward from the through hole so as to overlap the insulating portion, and the thickness of the extension portion decreases toward an outer circumference of the extension portion.

In the gas sensor element (1) above, the electrolyte portion has an extension portion that extends outward from the through hole so as to overlap the insulating portion. However, since the first insulating surface is flush with the first electrolyte surface, the occurrence of cracking or breakage of the first conductor layer formed so as to extend continuously from the first insulating surface to the first electrolyte surface can be suppressed.

In a preferred embodiment (2) of the gas sensor element (1) above, a side wall portion of the insulating portion which defines the through hole has an outwardly convex arcuate surface on the side where the first insulating surface is present.

In (2) above, no sharp edge is formed in a region in which the electrolyte portion and the insulating portion overlap each other on the first insulating surface side of the insulating portion. This configuration can mitigate stress concentration on the boundary between the electrolyte portion and the insulating portion on the first insulating surface side. Therefore, the occurrence of cracking of the extension portion that begins from a point on the boundary between the electrolyte portion and the insulating portion can be suppressed, whereby the durability of the gas sensor element can be improved.

The present invention can be embodied in various forms other than a gas sensor element. For example, the present invention can be embodied as a gas sensor including the gas sensor element (1) or (2) above, and in the form of a method of manufacturing the gas sensor element or the gas sensor.

DESCRIPTION OF REFERENCE NUMERALS

Figure 1:
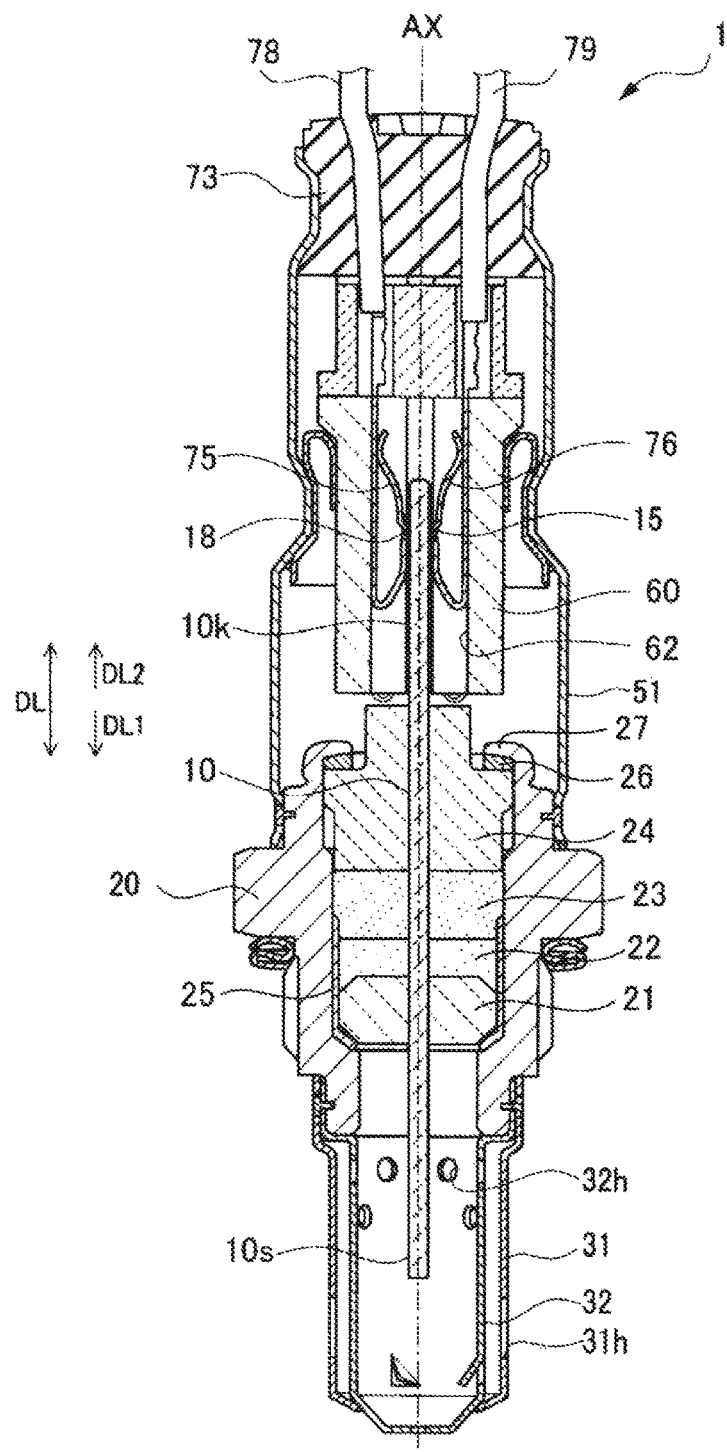
FIG. 1 is a longitudinal cross-sectional view of a gas sensor cut along an axial line.

Reference numerals used to identify various features in the drawings include the following, 1: gas sensor
10, 410: gas sensor element
14 to 18: pad
20: metallic shell
21: ceramic holder
22, 23: packed powder layer
24: ceramic sleeve
25: metallic holder
26: crimp packing
31: outer protector
32: inner protector
31h, 32h: gas introduction hole
51: outer tube
60: separator
62: insertion hole
73: grommet
75: terminal member
78, 79: lead wire
111: composite ceramic layer for detection
112: insulating portion for detection
112h: through hole
113: first insulating surface
114: second insulating surface
131: electrolyte portion for detection
133: first electrolyte surface
134: second electrolyte surface
135: extension portion
136: first extending surface
137: side wall portion
150: first conductor layer
151: first electrode layer
152: first lead layer
155: second conductor layer
156: second electrode layer
157: second lead layer
160: protective layer
161: protective portion
161h: through hole
161m, 161n, 161p: through hole
162: porous portion
170: insulating layer
170h: through hole
171: main portion
172: porous portion
180: heater layer
181: heater conductor
182, 183: insulating layer
211: composite ceramic layer for pumping
212: insulating portion for pumping
212h: through hole
213: first insulating surface
214: second insulating surface
231: electrolyte portion for pumping
233: first electrolyte surface
234: second electrolyte surface
250: first conductor layer
251: first electrode layer
252: first lead layer
255: second conductor layer
256: second electrode layer
257: second lead layer
305: punch
306: forward end portion
307: inclined portion
411: composite ceramic layer
412: insulating portion
412h: through hole
412m: through hole
413: first insulating surface
414: second insulating surface
416: sensor pad
431: electrolyte portion
433: first electrolyte surface
434: second electrolyte surface
435: extension portion
436: first extending surface
437: side wall portion
450: first conductor layer
451: first electrode portion
452: first lead portion
455: second conductor layer
456: second electrode portion
457: second lead portion
460: protective layer
461: protective portion
461h: through hole
461n: through hole
462: porous portion
470: introduction path formation layer
475: introduction groove
476: reference chamber groove
477: gas flow groove
551: first electrode layer
AX: axial line
GD: gas introduction path
AD: ambient air introduction path
SP: measurement chamber
TR: gas flow path
KS: reference chamber

DETAILED DESCRIPTION OF THE PREFERRED EMBODIMENTS

The invention will now be described with reference to the drawings. However, the present invention should not be construed as being limited thereto.

A. First Embodiment

FIG. 1 is a longitudinal cross-sectional view of a gas sensor 1 according to a first embodiment of the present invention that is cut along an axial line AX. The gas sensor 1 is attached to, for example, an exhaust pipe of an internal combustion engine and used as an oxygen sensor. In the following description, the lower side of the gas sensor 1 in FIG. 1 is referred to as a forward end side DL1, and the upper side is referred to as a rear end side DL2.

The gas sensor 1 includes, as main components, a gas sensor element 10 and a metallic shell 20. The gas sensor element 10 is a plate-shaped element extending in a longitudinal direction DL and is configured to detect the concentration of oxygen in exhaust gas, which is a measurement gas. The gas sensor element 10 is disposed in the gas sensor 1 such that the center line of the gas sensor element 10 extending in the longitudinal direction DL coincides with the axial line AX.

The metallic shell 20 is a tubular metallic member for holding the gas sensor element 10 therein. The metallic shell 20 holds the gas sensor element 10 with a forward end portion 10s of the gas sensor element 10 protruding forward from the metallic shell 20 and a rear end portion 10k of the gas sensor element 10 protruding rearward from the metallic shell 20. An outer protector 31 and an inner protector 32, which are formed of metal, are disposed at the forward end of the metallic shell 20 and cover the forward end portion 10s of the gas sensor element 10. The outer protector 31 has a plurality of gas introduction holes 31*h*, and the inner protector 32 has a plurality of gas introduction holes 32*h*. The measurement gas is introduced from the outside of the outer protector 31 through the gas introduction holes 31*h* and 32*h* into a space around the forward end portion 10*s* of the gas sensor element 10 disposed inside the inner protector 32.

An annular ceramic holder 21, packed powder layers 22 and 23 (hereinafter also referred to as talc rings 22 and 23), and a ceramic sleeve 24 are disposed in this order from the forward end side DL1 toward the rear end side DL2 within the metallic shell 20 so as to surround the outer circumference of the gas sensor element 10. A metallic holder 25 is disposed around the ceramic holder 21 and the outer circumference of the talc ring 22. A crimp packing 26 is disposed at the rear end of the ceramic sleeve 24. A rear end portion 27 of the metallic shell 20 is crimped such that the ceramic sleeve 24 is pressed toward the forward end side through the crimp packing 26.

A cylindrical outer tube 51 is disposed at the rear end of the metallic shell 20 so as to surround the rear end portion 10*k* of the gas sensor element 10. A separator 60 is disposed inside the outer tube 51. The separator 60 surrounds the circumference of the rear end portion 10*k* of the gas sensor element 10 and holds five terminal members 75 and 76 (only two of them are shown in FIG. 1) attached to the forward ends of five lead wires 78 and 79 (only two of them are shown in FIG. 1) such that the five terminal members 75 and 76 are spaced apart from each other. The separator 60 has an insertion hole 62 extending therethrough in the direction of the axial line AX. The rear end portion 10*k* of the gas sensor element 10 is inserted into the insertion hole 62. The five terminal members 75 and 76 are disposed within the insertion hole 62 so as to be spaced apart from each another. The five terminal members 75 and 76 elastically abut against respective pads 14 to 18, described below, of the gas sensor element 10 and are electrically connected thereto. A grommet 73 that seals a rear end opening of the outer tube 51 is fitted into the rear end of the outer tube 51. The five lead wires 78 and 79 pass through the grommet 73.

Figure 2:
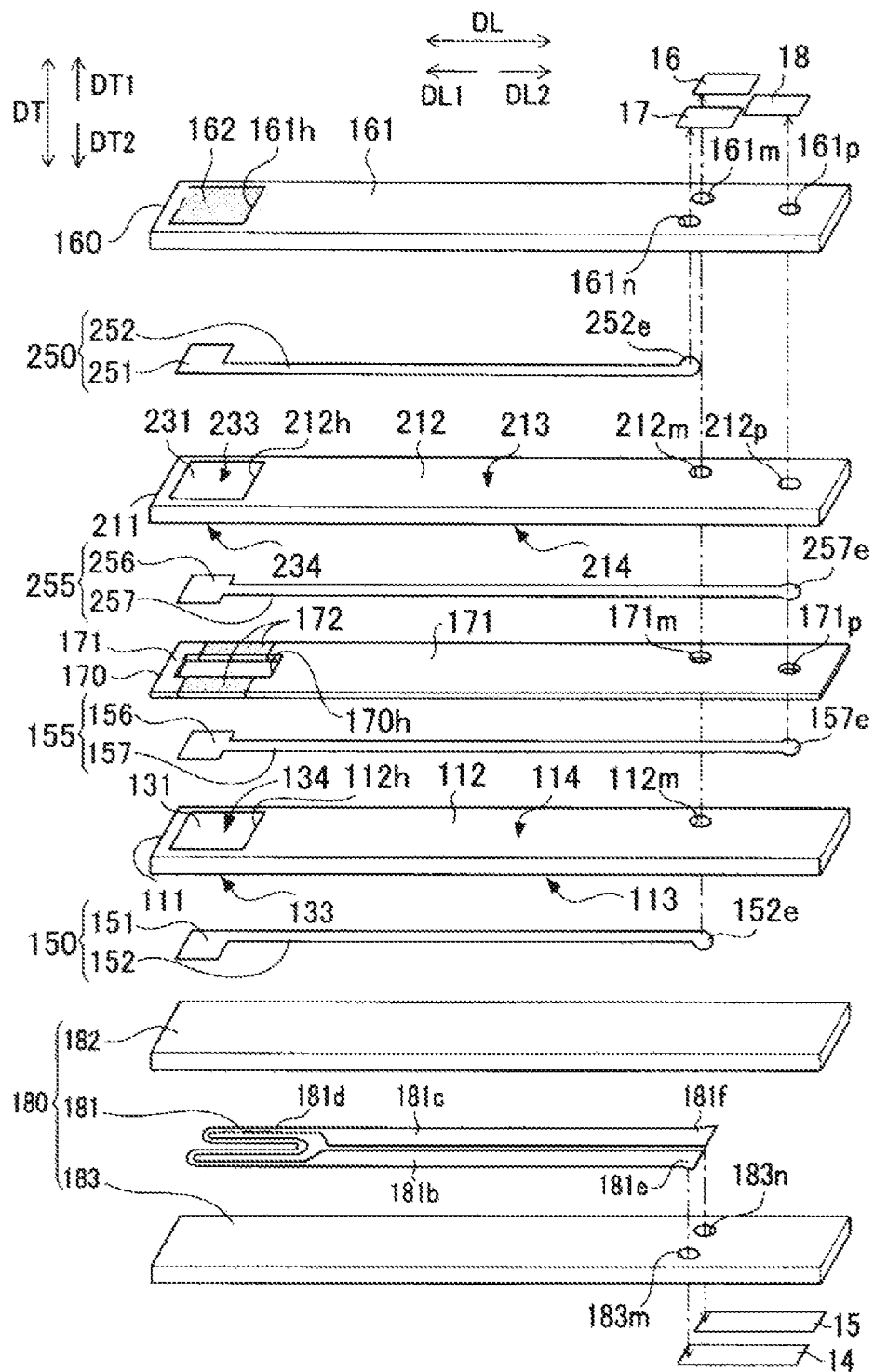
FIG. 2 is an exploded perspective view of a gas sensor element according to a first embodiment.
Figure 3:
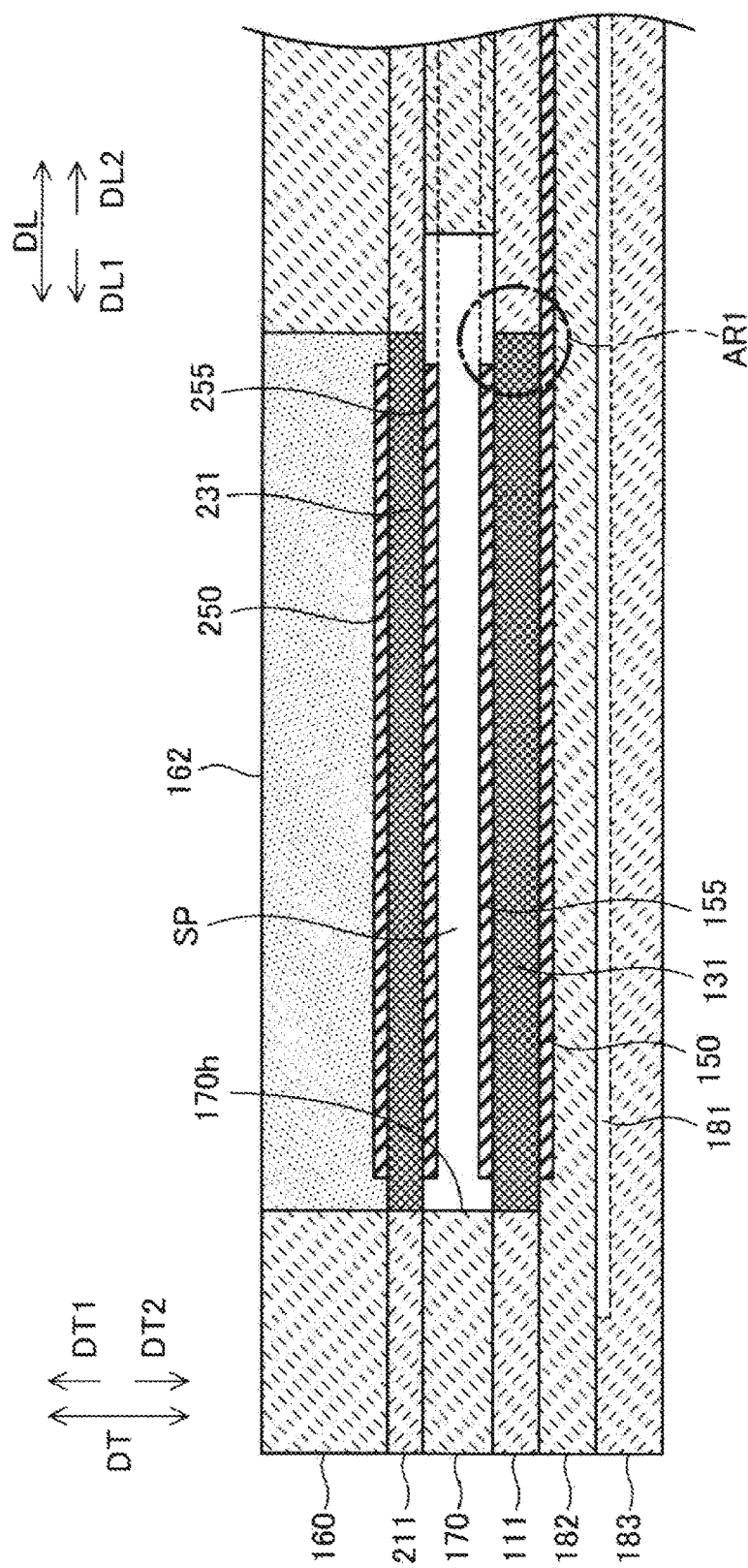
FIG. 3 is a schematic cross-sectional view illustrating a stacking state of the components of the gas sensor element according to the first embodiment.

FIG. 2 is an exploded perspective view of the gas sensor element 10. FIG. 3 is a schematic cross-sectional view illustrating the stacking state of the components of the gas sensor element 10. In FIGS. 2 and 3, the left side corresponds to the forward end side DL1 of the gas sensor 1, and the right side corresponds to the rear end side DL2.

The gas sensor element 10 includes a plurality of ceramic layers and conductor layers stacked in a thickness direction DT. Specifically, the gas sensor element 10 includes: a composite ceramic layer 111 that is used to detect the concentration of oxygen in the measurement gas; and a composite ceramic layer 211 for pumping that is disposed on one side DT1, with respect to the thickness direction, of the composite ceramic layer 111 for detection and is used to control the oxygen concentration of the measurement gas in a measurement chamber SP (see FIG. 3). An insulating layer 170 is disposed between the composite ceramic layer 111 for detection and the composite ceramic layer 211 for pumping. A first conductor layer 150 is formed on the other side DT2, with respect to the thickness direction, of the composite ceramic layer 111 for detection, and a second conductor layer 155 is formed on the one side DT1 of the composite ceramic layer 111 for detection. A first conductor layer 250 is formed on the one side DT1 of the composite ceramic layer 211 for pumping, and a second conductor layer 255 is formed on the other side DT2 of the composite ceramic layer 211 for pumping. A heater layer 180 is stacked on the other side DT2 of the composite ceramic layer 111 for detection and the first conductor layer 150, and a protective layer 160 is stacked on the one side DT1 of the composite ceramic layer 211 for pumping and the first conductor layer 250.

The composite ceramic layer 111 for detection includes: a rectangular plate-shaped insulating portion 112 for detection that is formed of an insulating ceramic (e.g., alumina) and has a through hole 112*h* having a rectangular shape in plan view and passing through the insulating portion 112 in the thickness direction DT; and a plate-shaped electrolyte portion 131 for detection that is formed of a solid electrolyte ceramic (zirconia) and disposed within the through hole 112*h* of the insulating portion 112 for detection. The insulating portion 112 for detection has a first insulating surface 113 facing the other side DT2 and a second insulating surface 114 facing the one side DT1. The electrolyte portion 131 for detection has a first electrolyte surface 133 facing the other side DT2 and a second electrolyte surface 134 facing the one side DT1.

The first conductor layer 150 includes: a rectangular first electrode layer 151 that is formed on the first electrolyte surface 133 of the electrolyte portion 131 for detection so as to be smaller than the opening area of the through hole 112*h*; and a strip-shaped first lead layer 152 extending from the first electrode layer 151 toward the rear end side DL2 with respect to the longitudinal direction. The first lead layer 152 extends on the first electrolyte surface 133 and the first insulating surface 113 continuously from the first electrolyte surface 133 to the first insulating surface 113. As does the first conductor layer 150, the second conductor layer 155 includes: a rectangular second electrode layer 156 formed on the second electrolyte surface 134 of the electrolyte portion 131 for detection so as to be smaller than the opening area of the through hole 112*h*; and a strip-shaped second lead layer 157 extending from the second electrode layer 156 toward the rear end side DL2. The second lead layer 157 extends on the second electrolyte surface 134 and the second insulating surface 114 continuously from the second electrolyte surface 134 to the second insulating surface 114.

The composite ceramic layer 211 for pumping includes: a rectangular plate-shaped insulating portion 212 for pumping that is formed of an insulating ceramic (alumina) and has a through hole 212*h* having a rectangular shape in plan view and passing through the insulating portion 212 in the thickness direction DT; and a plate-shaped electrolyte portion 231 for pumping that is formed of a solid electrolyte ceramic (zirconia) and disposed within the through hole 212*h* of the insulating portion 212 for pumping. The insulating portion 212 for pumping has a first insulating surface 213 facing the one side DT1 with respect to the thickness direction and a second insulating surface 214 facing the other side DT2 with respect to the thickness direction. The electrolyte portion 231 for pumping has a first electrolyte surface 233 facing the one side DT1 and a second electrolyte surface 234 facing the other side DT2.

The first conductor layer 250 includes: a rectangular first electrode layer 251 formed on the first electrolyte surface 233 of the electrolyte portion 231 for pumping so as to be smaller than the opening area of the through hole 212*h*; and a strip-shaped first lead layer 252 extending from the first electrode layer 251 toward the rear end side DL2. The first lead layer 252 extends on the first electrolyte surface 233 and the first insulating surface 213 continuously from the first electrolyte surface 233 to the first insulating surface 213. As does the first conductor layer 250, the second conductor layer 255 includes: a rectangular second electrode layer 256 formed on the second electrolyte surface 234 of the electrolyte portion 231 for pumping so as to be smaller than the opening area of the through hole 212h; and a strip-shaped second lead layer 257 extending from the second electrode layer 256 toward the rear end side DL2. The second lead layer 257 extends on the second electrolyte surface 234 and the second insulating surface 214 continuously from the second electrolyte surface 234 to the second insulating surface 214.

The insulating layer 170 has a rectangular through hole 170h that extends through the insulating layer 170 so as to overlap the through holes 112h and 212h. The through hole 170h is surrounded by the insulating layer 170, the composite ceramic layer 111 for detection (the electrolyte portion 131 for detection), and the composite ceramic layer 211 for pumping (the electrolyte portion 231 for pumping) and thereby forms the hollow measurement chamber SP. The insulating layer 170 includes a main portion 171 formed of dense alumina and two porous portions 172. The two porous portions 172 are formed of a porous ceramic, form parts of two opposite walls of the through hole 170h that extend in the longitudinal direction DL, and are exposed to the outside on opposite sides with respect to the lateral direction (direction perpendicular to the longitudinal direction DL and to the thickness direction DT). The porous portions 172 are diffusion controlling layers that allow the measurement gas to be introduced from the outside of the gas sensor element 10 into the measurement chamber SP under prescribed rate-controlling conditions.

The protective layer 160 is stacked on the one side DT1 (with respect to the thickness direction) of the composite ceramic layer 211 for pumping so as to cover the first conductor layer 250. The protective layer 160 includes: a porous portion 162 that covers the first electrode layer 251 and the electrolyte portion 231 for pumping; and a protective portion 161. The protective portion 161 is formed of a dense ceramic, covers the insulating portion 212 for pumping so as to protect the insulating portion 212, and has a through hole 161h that accommodates the porous portion 162.

Three sensor pads 16, 17, and 18 that are configured to be in contact with three terminal members 75 (see FIG. 1) are formed on the protective portion 161. The sensor pad 16 electrically communicates with an end portion 152e of the first conductor layer 150 (the first lead layer 152) that is located on the rear end side DL2 via through holes 161m, 212m, 171m, and 112m. The sensor pad 17 electrically communicates with an end portion 252e of the first conductor layer 250 (the first lead layer 252) that is located on the rear end side DL2 via a through hole 161n. The sensor pad 18 electrically communicates with an end portion 157e of the second conductor layer 155 (the second lead layer 157) and an end portion 257e of the second conductor layer 255 (the second lead layer 257) via through holes 161p, 212p, and 171p.

The heater layer 180 includes two plate-shaped insulating layers 182 and 183 formed of alumina and a heater conductor 181 sandwiched between the insulating layers 182 and 183. The heater conductor 181 has: a meandering heat-generating portion 181d; and first and second lead portions 181b and 181c that are connected to opposite ends of the heat-generating portion 181d and extend in a straight line. Two heater pads 14 and 15 configured to be in contact with two terminal members 76 (see FIG. 1) are formed on the other side DT2 of the insulating layer 183. The heater pad 14 electrically communicates with an end portion 181e of the first lead portion 181b that is located on the rear end side DL2 via a through hole 183m. The heater pad 15 electrically communicates with an end portion 181f of the second lead portion 181c that is located on the rear end side DL2 via a through hole 183n.

In the gas sensor element 10 according to the present embodiment, oxygen is initially supplied to the porous first electrode layer 151 to form a reference gas. Then, the direction and magnitude of current flowing between the first electrode layer 251 and the second electrode layer 256 sandwiching the electrolyte portion 231 for pumping therebetween are adjusted, through the three lead wires 78 electrically communicating with the sensor pads 16 to 18, so as to pump oxygen from the measurement chamber SP into the porous portion 162 or from the porous portion 162 into the measurement chamber SP through the electrolyte portion 231 such that the potential difference between the first electrode layer 151 and the second electrode layer 156 sandwiching the electrolyte portion 131 for detection therebetween becomes equal to a prescribed value (i.e., the concentration of oxygen in the measurement chamber SP becomes constant). The magnitude of the current flowing between the first electrode layer 251 and the second electrode layer 256 corresponds to the concentration of oxygen in the measurement gas that flows into the measurement chamber SP through the porous portions 172, so that the concentration of oxygen in the measurement gas can be detected from the magnitude of the current. During measurement of the oxygen concentration, a current is supplied to the heater conductor 181 through the two lead wires 79 electrically communicating with the heater pads 14 and 15 to generate heat, and the electrolyte portion 131 for detection and the electrolyte portion 231 for pumping are thereby heated and activated.

Figure 4:
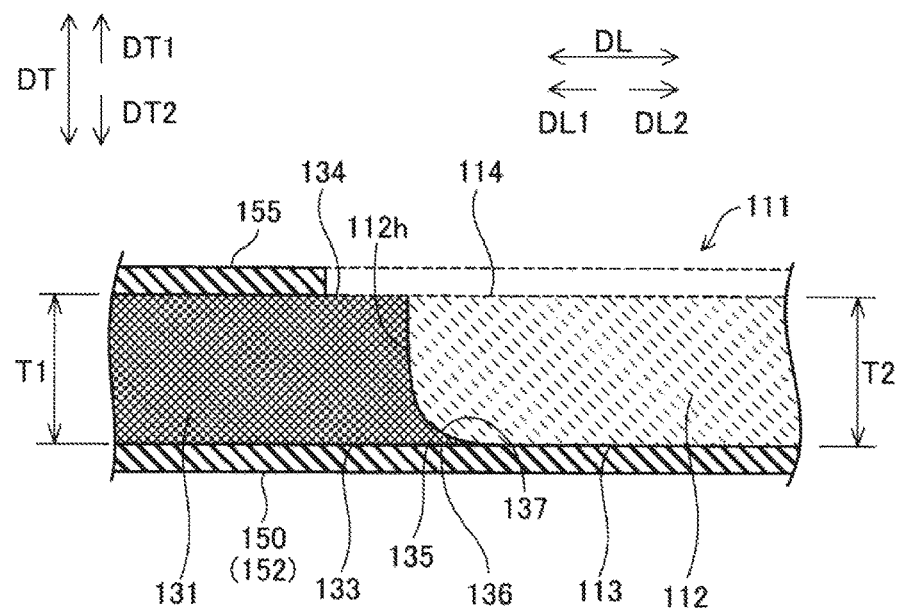
FIG. 4 is a view showing, on an enlarged scale, a cross-sectional portion AR1 shown in FIG. 3 and a vicinity thereof.

FIG. 4 is a view showing, on an enlarged scale, a cross-sectional portion AR1 shown in FIG. 3 and a vicinity thereof. FIG. 4 shows the structure of a portion of the composite ceramic layer 111 for detection of the gas sensor element 10 according to the present embodiment, the portion including the boundary between the electrolyte portion 131 for detection and the insulating portion 112 for detection. As shown in FIG. 4, in the present embodiment, the thickness T1 of the electrolyte portion 131 for detection is substantially the same as the thickness T2 of the insulating portion 112 for detection. In addition, the first insulating surface 113 and the first electrolyte surface 133 are flush with each other. In a cross section of the composite ceramic layer 111 for detection obtained by cutting the composite ceramic layer 111 in the thickness direction DT, the electrolyte portion 131 for detection has, on the first electrolyte surface 133 side, an extension portion 135 extending outward from the through hole 112h so as to overlap the insulating portion 112 for detection in the thickness direction DT. The thickness of the extension portion 135 decreases toward the outer circumference of the extension portion 135. The outer circumference of the extension portion 135 is continuously connected to the first insulating surface 113. A first extending surface 136 of the extension portion 135 that is a surface thereof on the other side DT2 is included in the first electrolyte surface 133 and continuously connects the first insulating surface 113 to the first electrolyte surface 133. Therefore, the first insulating surface 113, the first extending surface 136, and the first electrolyte surface 133 are connected to one another so as to form a single flat surface with no steps. A side wall portion 137 of the insulating portion 112 for detection which defines the through hole 112h has an outwardly convex arcuate surface on the side where the first insulating surface 113 is present. Specifically, on the first insulating surface 113 side, the opening area of the through hole 112h increases from the inner side in the thickness direction toward the outer side. The structure shown in FIG. 4 is formed over the entire outer circumference of the electrolyte portion 131 for detection.

Figure 5:
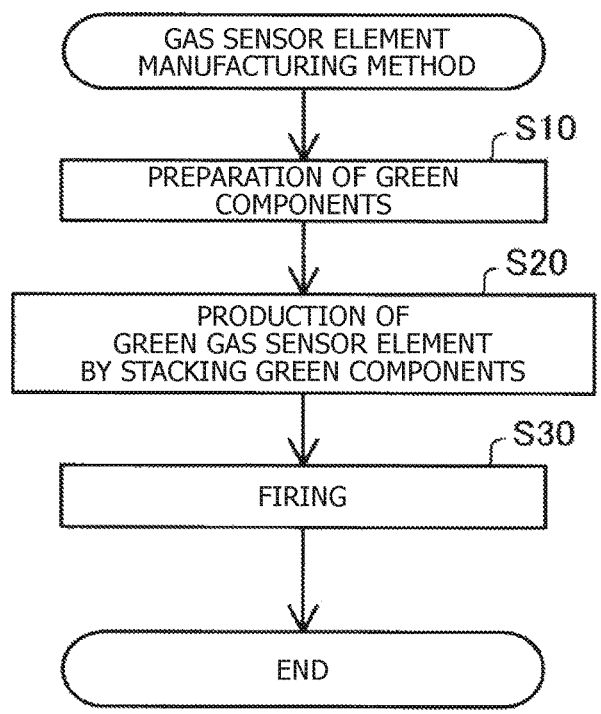
FIG. 5 is a flowchart showing a method of manufacturing the gas sensor element.

FIG. 5 is a flowchart showing a method of manufacturing the gas sensor element 10. In the following description, the same reference numerals are used for members after firing and corresponding members before firing, for the sake of convenience. In the manufacturing method in the present embodiment, first, green members corresponding to the components of the gas sensor element 10 are prepared (step S10). Specifically, a green protective layer 160, a green composite ceramic layer 211 for pumping, a green insulating layer 170, a green composite ceramic layer 111 for detection, and green insulating layers 182 and 183 are prepared. See FIG. 3. A method of producing the composite ceramic layer 211 for pumping and the composite ceramic layer 111 for detection will be described below.

After preparing the green members, the prepared green members are stacked in the order shown in FIG. 2 to produce a green gas sensor element 10 (step S20). Before step S20, a green heater conductor 181 is formed on the one side DT1 of the green insulating layer 183 or the other side DT2 of the green insulating layer 182 by screen printing.

After the green gas sensor element 10 is produced in step S20 above, the green gas sensor element 10 is fired by a known method (step S30). The gas sensor element 10 is thereby completed through the above steps.

Figure 6:
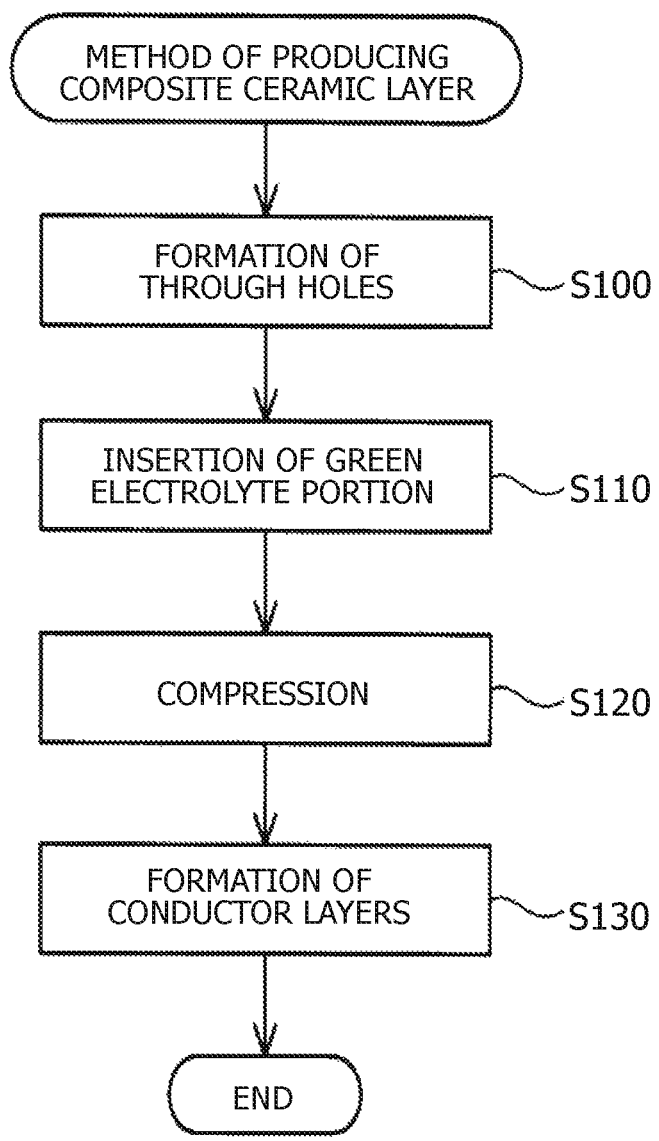
FIG. 6 is a flowchart showing a method of producing a composite ceramic layer.

FIG. 6 is a flowchart showing a method of producing the green composite ceramic layer 111 for detection and the green composite ceramic layer 211 for pumping that are prepared in step S10 in FIG. 5. FIGS. 7A to 7D are a series of illustrations for explaining the production method shown in FIG. 6. The method of producing the green composite ceramic layer 211 for pumping is the same as the method of producing the green composite ceramic layer 111 for detection. Therefore, the method of producing the green composite ceramic layer 111 for detection will be described, and the description of the method of producing the green composite ceramic layer 211 for pumping will be omitted.

First, a green insulating portion sheet (green insulating sheet) 112s having a thickness of 155±20 μm and a green electrolyte portion sheet (green electrolyte sheet) thicker than the green insulating portion sheet, i.e., having a thickness of 200±20 μm, are prepared in advance. These sheets are prepared using a doctor blade method. Then a through hole 112h is formed in the green insulating portion sheet 112s (step S100). When the thickness of the green insulating portion sheet 112s is set to 155±20 μm and the thickness of the green electrolyte portion sheet is set to 200±20 μm, the thickness of the green electrolyte portion sheet becomes larger by at least 5 μm than the thickness of the green insulating portion sheet 112s.

Figure 7A:
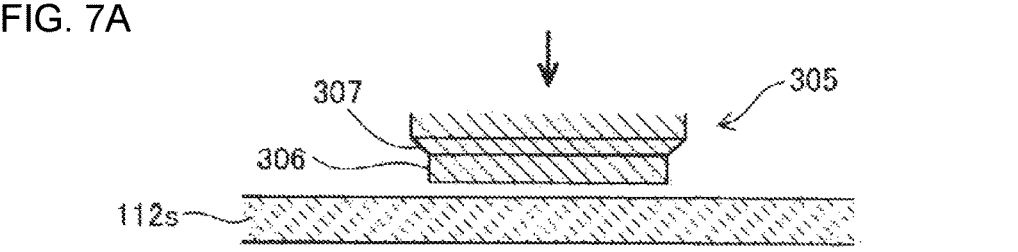
FIGS. 7A to 7D are a series of steps illustrating the production method shown in FIG. 6.
Figure 7B:
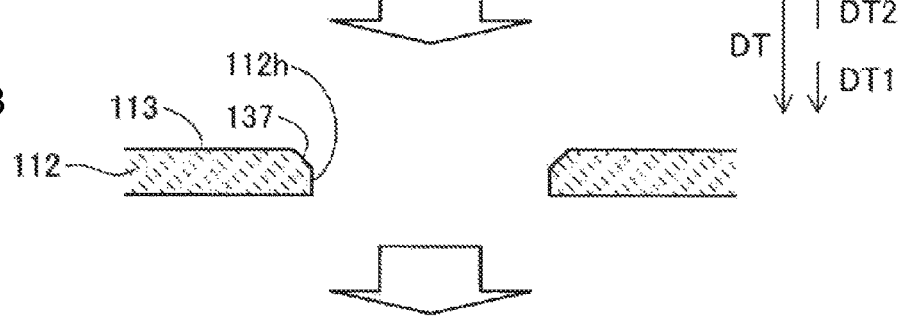

FIGS. 7A and 7B show the manner of forming the through hole 112h in the green insulating portion sheet 112s. In the present embodiment, a punch 305 is used to form the through hole 112h in the green insulating portion sheet 112s. The punch 305 includes: a forward end portion 306 having a rectangular shape in plan view and disposed on the side toward the green insulating portion sheet 112s; and an inclined portion 307 disposed on the side opposite to the green insulating portion sheet 112s. The inclined portion 307 is configured such that the area of its cross section perpendicular to the thickness direction DT increases from the cross-sectional area of the forward end portion 306 as the distance from the forward end portion 306 in the thickness direction DT increases. When the through hole 112h is formed in the green insulating portion sheet 112s by the punch 305, a green side wall portion 137 of the green insulating portion sheet 112s defining the through hole 112h is chamfered, by the inclined portion 307 of the punch 305, on the side where a green first insulating surface 113 is present. A green insulating portion 112 is thereby formed. The method of forming the through hole 112h is not limited to the method described above. For example, a punch having a rectangular shape in plan view may be used to form a through hole in the green insulating portion sheet 112s, and then another jig may be used to chamfer the green side wall portion 137. The chamfered side wall portion 137 may have a flat surface as shown in FIG. 7B or may have a rounded surface.

Figure 7C:
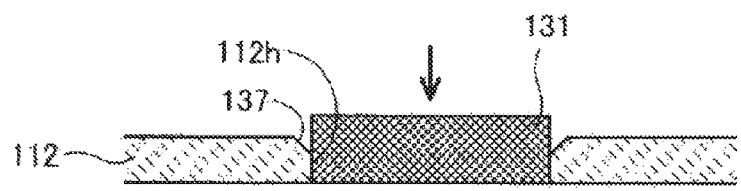

Next, as shown in FIG. 7C, a green electrolyte portion 131 punched from the green electrolyte portion sheet is inserted into the through hole 112h formed in the green insulating portion 112 (step S110 in FIG. 6). As described above, the green electrolyte portion sheet is thicker than the green insulating portion sheet 112s. Therefore, when the green electrolyte portion 131 is inserted into the through hole 112h of the green insulating portion 112, part of the green electrolyte portion 131 protrudes from the through hole 112h.

Figure 7D:
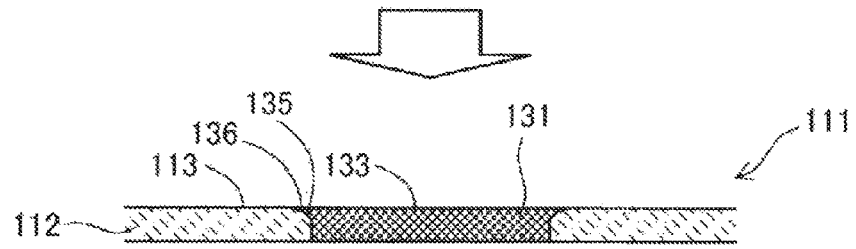

After the green electrolyte portion 131 is inserted into the through hole 112h, the green insulating portion 112 and the green electrolyte portion 131 are compressed simultaneously in the thickness direction DT such that the green first insulating surface 113 becomes flush with the green first electrolyte surface 133 (step S120 in FIG. 6). The part of the green electrolyte portion 131 that protrudes from the through hole 112h thereby spreads outward along the chamfered green side wall portion 137. Then, as shown in FIG. 7D, a green extension portion 135 that extends outward from the through hole 112h so as to overlap the green insulating portion 112 and has a thickness decreasing toward the outer circumference of the green extension portion 135 is formed on the green first electrolyte surface 133 side of the green electrolyte portion 131. As a result of the compression, the outer circumference of the green extension portion 135 is continuously connected to the green first insulating surface 113, and a green first extending surface 136 of the green extension portion 135 that is a surface thereof on the other side DT2 continuously connects the green first insulating surface 113 to the green first electrolyte surface 133. The green side wall portion 137 defining the through hole 112h has an arcuate surface on the side where the green first insulating surface 113 is present. Through the steps described above, the green composite ceramic layer 111 for detection including the green electrolyte portion 131 and the green insulating portion 112 is completed. The green composite ceramic layer 111 for detection shown in FIG. 7D is turned upside down and then stacked in the manner shown in FIG. 3.

Preferably, the compression process in step S120 shown in FIG. 6 is performed in a temperature environment of 60° C. or higher and preferably 80° C. or higher and 100° C. or lower. When the compression is performed in the above-described temperature environment, both the green insulating portion 112 and the green electrolyte portion 131 are softened. This allows the green first electrolyte surface 133 of the green electrolyte portion 131 and the green first insulating surface 113 of the green insulating portion 112 to be smoothly connected to each other and also allows the green extension portion 135 to be easily formed.

After completing the compression process, conductor layers are formed (step S130 in FIG. 6). Specifically, a green first conductor layer 150 (a green first electrode portion 151 and a green first lead portion 152) is formed by screen printing so as to extend continuously from the green first electrolyte surface 133 of the green electrolyte portion 131 (see FIG. 4) to the green first insulating surface 113 of the green insulating portion 112. Then a green second conductor layer 155 (a green second electrode portion 156 and a green second lead portion 157) is formed by screen printing so as to extend continuously from a green second insulating surface 114 of the green insulating portion 112 to a green second electrolyte surface 134 of the green electrolyte portion 131. Through the steps described above, the green composite ceramic layer 111 for detection is completed. The green composite ceramic layer 211 for pumping can be completed through the same steps.

As shown in FIG. 4, in the gas sensor element 10 in the present embodiment described above, the extension portion 135 that extends outward from the through hole 112h so as to overlap the insulating portion 112 for detection is formed in the electrolyte portion 131 for detection disposed in the through hole 112h of the insulating portion 112 for detection. In the present embodiment, the first electrolyte surface 133 including the first extending surface 136 that is a surface of the extension portion 135 on the other side DT2 is flush with the first insulating surface 113. Therefore, the occurrence of cracking or breakage of the first conductor layer 150 formed so as to extend continuously from the first insulating surface 113 to the first electrolyte surface 133 can be suppressed.

In the present embodiment, the extension portion 135 is formed. Therefore, on the first insulating surface 113 side, the opening area of the through hole 112h increases from the inner side in the thickness direction toward the outer side. This can prevent the electrolyte portion 131 for detection disposed in the through hole 112h from easily becoming dislodged from the through hole 112h during production of the gas sensor element 10.

In the present embodiment, the side wall portion 137 of the insulating portion 112 for detection that defines the through hole 112h (see FIG. 4) has an outwardly convex arcuate surface on the side where the first insulating surface 113 is present. Therefore, no sharp edge is formed in a region in which the electrolyte portion 131 for detection and the insulating portion 112 for detection overlap on the first insulating surface 113 side. This can mitigate stress concentration on the boundary between the electrolyte portion 131 for detection and the insulating portion 112 for detection on the first insulating surface 113 side. Therefore, the occurrence of cracking of the extension portion 135 that starts from a point on the boundary between the electrolyte portion 131 for detection and the insulating portion 112 for detection can be suppressed, whereby the durability of the gas sensor element 10 can be improved.

In the present embodiment, the extension portion 135 extending outward is formed in the electrolyte portion 131 for detection, but the effective area of the through hole 112h formed in the insulating portion 112 for detection is almost unchanged. Therefore, variations in gas detection performance of the gas sensor elements 10 due to variations in the production environment, etc., can be suppressed.

In the present embodiment, the composite ceramic layer 211 for pumping is produced using the same production method as that for the composite ceramic layer 111 for detection, so that the surface of the composite ceramic layer 211 for pumping that is located on the one side DT1 has the same structure as that shown in FIG. 4. Therefore, the first insulating surface 213 of the composite ceramic layer 211 for pumping is flush with the first electrolyte surface 233, so that the occurrence of cracking or breakage of the first conductor layer 250 disposed on the one side DT1 of the composite ceramic layer 211 for pumping can be suppressed. The structure in FIG. 4 may be applied to only one of the composite ceramic layer 111 for detection and the composite ceramic layer 211 for pumping. Specifically, one of the composite ceramic layer 111 for detection and the composite ceramic layer 211 for pumping may have a structure in which its electrolyte portion and insulating portion have the same thickness and no extension portion is formed.

In the present embodiment, the extension portion 135 is formed on the surface of the composite ceramic layer 111 for detection that is located on the other side DT2. However, the extension portion 135 may be formed on the surface on the one side DT1. The extension portion 135 may be formed on each of the opposite surfaces of the composite ceramic layer 111 for detection that are located on the one side DT1 and the other side DT2.

B. Second Embodiment

In the first embodiment described above, a description has been given of the two-cell type gas sensor element 10 including two composite ceramic layers (the composite ceramic layer 111 for detection and the composite ceramic layer 211 for pumping). The structure of the gas sensor element 10 shown in FIG. 4 is similarly applicable to a one-cell type gas sensor element including one composite ceramic layer.

Figure 8:
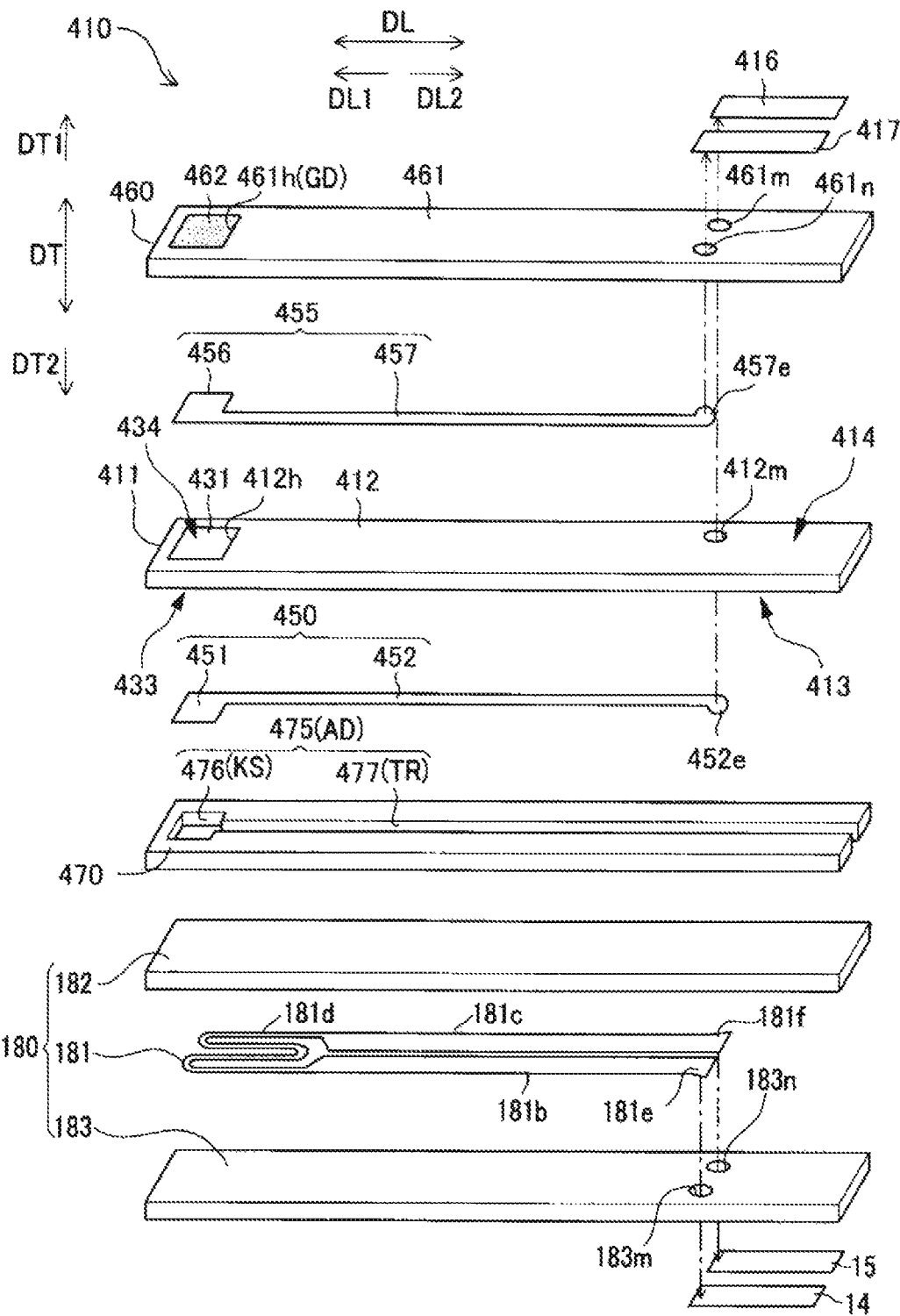
FIG. 8 is an exploded perspective view of a gas sensor element according to a second embodiment.
Figure 9:
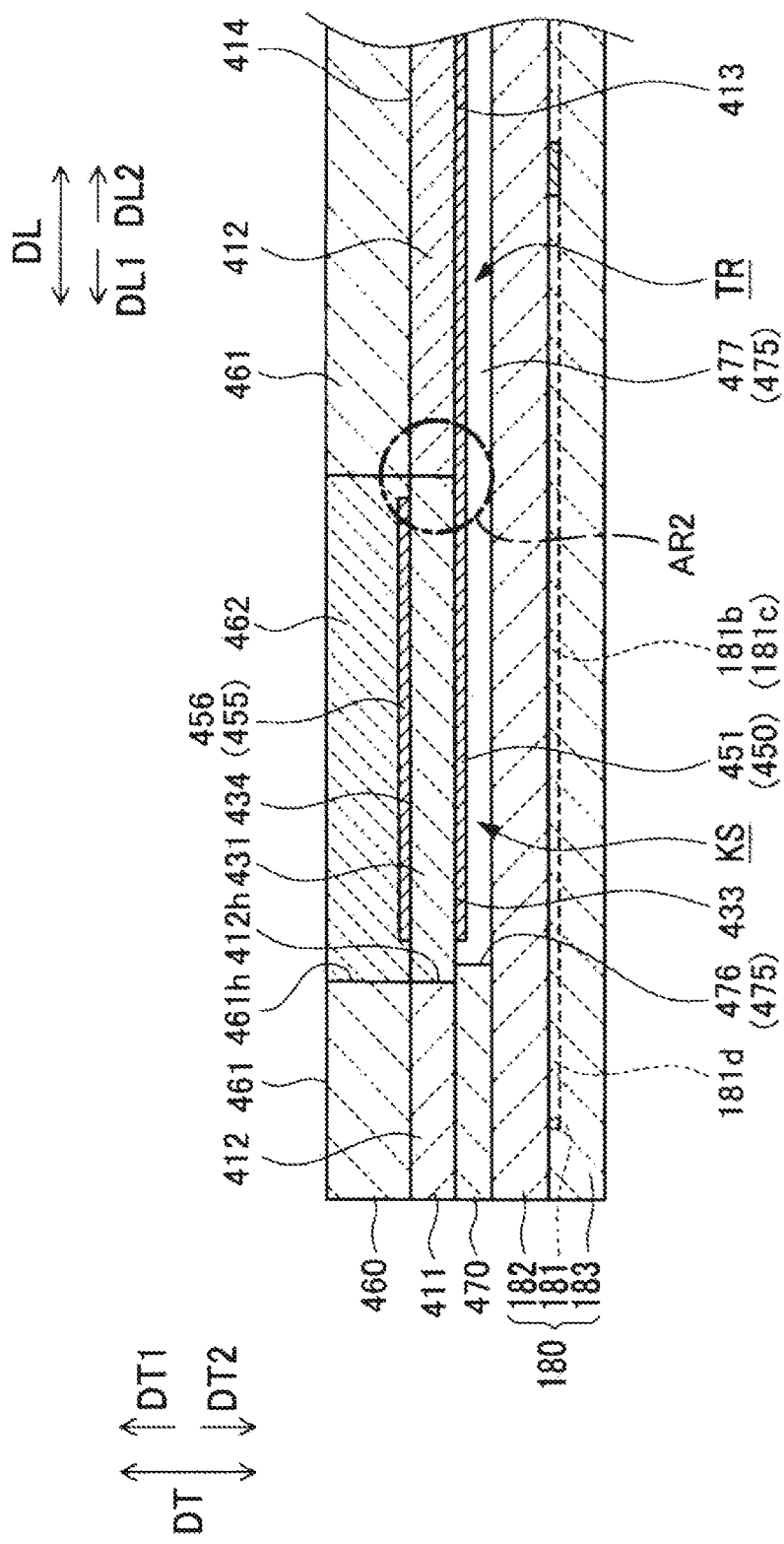
FIG. 9 is a schematic cross-sectional view illustrating the stacking state of the components of the gas sensor element in the second embodiment.

FIG. 8 is an exploded perspective view of a one-cell type gas sensor element 410. FIG. 9 is a schematic cross-sectional view illustrating the stacking state of the components of the gas sensor element 410. The structure of the gas sensor element 410 will next be described, with attention focused mainly on the differences from the gas sensor element 10 of the first embodiment. In FIGS. 8 and 9, the same components as those in the gas sensor element 10 of the first embodiment are denoted by the same numerals.

The gas sensor element 410 includes a composite ceramic layer 411. A second conductor layer 455 and a protective layer 460 are stacked in this order on one side DT1, with respect to the thickness direction, of the composite ceramic layer 411. A first conductor layer 450, an introduction path formation layer 470, and a heater layer 180 are stacked in this order on the other side DT2, with respect to the thickness direction, of the composite ceramic layer 411.

The composite ceramic layer 411 includes an insulating portion 412 having a through hole 412h and an electrolyte portion 431. The electrolyte portion 431 is embedded in the through hole 412h. The insulating portion 412 has a first insulating surface 413 facing the other side DT2 with respect to the thickness direction and a second insulating surface 414 facing the opposite side, i.e., the one side DT1 with respect to the thickness direction. The electrolyte portion 431 has a first electrolyte surface 433 facing the other side DT2 with respect to the thickness direction and a second electrolyte surface 434 facing the opposite side, i.e., the one side DT1 with respect to the thickness direction.

The first conductor layer 450 includes: a rectangular first electrode portion 451 that is formed on the first electrolyte surface 433 of the electrolyte portion 431 so as to be smaller than the opening area of the through hole 412h; and a strip-shaped first lead portion 452 extending from the first electrode portion 451 toward the rear end side DL2 with respect to the longitudinal direction. The first conductor layer 450 is formed so as to extend continuously from the first electrolyte surface 433 to the first insulating surface 413.

The second conductor layer 455 includes: a substantially rectangular second electrode portion 456 that is formed on the second electrolyte surface 434 of the electrolyte portion 431 so as to be smaller than the opening area of the through hole 412h; and a strip-shaped second lead portion 457 extending from the second electrode portion 456 toward the rear end side DL2 with respect to the longitudinal direction. The second conductor layer 455 is formed so as to extend continuously from the second electrolyte surface 434 to the second insulating surface 414.

The protective layer 460 is stacked on the one side DT1, with respect to the thickness direction, of the composite ceramic layer 411 so as to cover the second conductor layer 455. The protective layer 460 includes a porous portion 462 and a protective portion 461. The porous portion 462 is formed of a porous ceramic disposed on the second electrode portion 456 and the electrolyte portion 431 of the composite ceramic layer 411. The protective portion 461 is formed of a dense ceramic, has a through hole 461h that accommodates the porous portion 462, and covers the insulating portion 412 of the composite ceramic layer 411 to protect the insulating portion 412. The through hole 461h serves as a gas introduction path GD for introducing an external measurement gas into the second electrode portion 456.

Sensor pads 416 and 417 are disposed on the protective portion 461. The sensor pad 416 electrically communicates with an end portion 452e of the first conductor layer 450 that is located on the rear end side DL2 through through holes 461m and 412m. The sensor pad 417 electrically communicates with an end portion 457e of the second conductor layer 455 that is located on the rear end side DL2 through a through hole 461n.

The introduction path formation layer 470 is formed of a dense ceramic and has an introduction groove 475 that extends through the introduction path formation layer 470 in its thickness direction DT. The introduction groove 475 is surrounded by the introduction path formation layer 470, the composite ceramic layer 411, and the heater layer 180 (the insulating layer 182) and thereby forms an ambient air introduction path AD for introducing ambient air into the first electrode portion 451. More specifically, the introduction groove 475 includes: a reference chamber groove 476 having a rectangular shape in plan view; and a gas flow groove 477 that is smaller in width than the reference chamber groove 476, extends from the reference chamber groove 476 toward the rear end side DL2, and has an opening at the rear end (the right end in FIG. 10) of the introduction path formation layer 470. The reference chamber groove 476 is surrounded by the introduction path formation layer 470, the electrolyte portion 431 of the composite ceramic layer 411, and the heater layer 180 and thereby forms a reference chamber KS. The gas flow groove 477 is surrounded by the introduction path formation layer 470, the insulating portion 412 of the composite ceramic layer 411, and the heater layer 180 and thereby forms a gas flow path TR. The first electrode portion 451 formed on the electrolyte portion 431 is exposed to the reference chamber KS.

The gas sensor element 410 of the present embodiment is disposed in the gas sensor 1 shown in FIG. 1 in the same manner as in the gas sensor element 10 of the first embodiment. However, in the second embodiment, a filter in communication with the ambient air is disposed in the grommet 73 disposed at the rear end portion of the gas sensor 1. The ambient air is introduced into the gas flow groove 477 of the introduction path formation layer 470 through this filter. In the present embodiment, the number of heater pads 14 and 15 is the same as that in the first embodiment. However, the number of sensor pads 416 and 417 is two, which is smaller by 1 than that in the first embodiment. Therefore, in the present embodiment, the number of terminal members 75 and 76 shown in FIG. 1 is 4, which is smaller by 1 than that in the first embodiment, and the number of lead wires 78 and 79 is 4, which is smaller by 1 than that in the first embodiment.

In the gas sensor element 410 of the present embodiment, the ambient air around the rear end portion of the gas sensor element 410 reaches the first electrode portion 451 through the ambient air introduction path AD described above. The measurement gas around the forward end portion of the gas sensor element 410 reaches the second electrode portion 456 through the porous portion 462 disposed in the through hole 461h of the protective layer 460. The electrolyte portion 431 is disposed between the first electrode portion 451 and the second electrode portion 456. Therefore, when the concentration of oxygen in the ambient air in contact with the first electrode portion 451 is different from the concentration of oxygen in the measurement gas in contact with the second electrode portion 456, the first electrode portion 451, the electrolyte portion 431, and the second electrode portion 456 form an oxygen concentration cell, and a potential difference is generated between the first electrode portion 451 and the second electrode portion 456. Therefore, the concentration of oxygen in the measurement gas can be detected by obtaining a signal indicating the potential difference output through the two lead wires 78 that electrically communicate with the sensor pads 416 and 417. During the measurement of the oxygen concentration, a current is supplied to the heater conductor 181 through the two lead wires 79 that electrically communicate with the heater pads 14 and 15 to generate heat, and the electrolyte portion 431 is thereby heated and activated.

Figure 10:
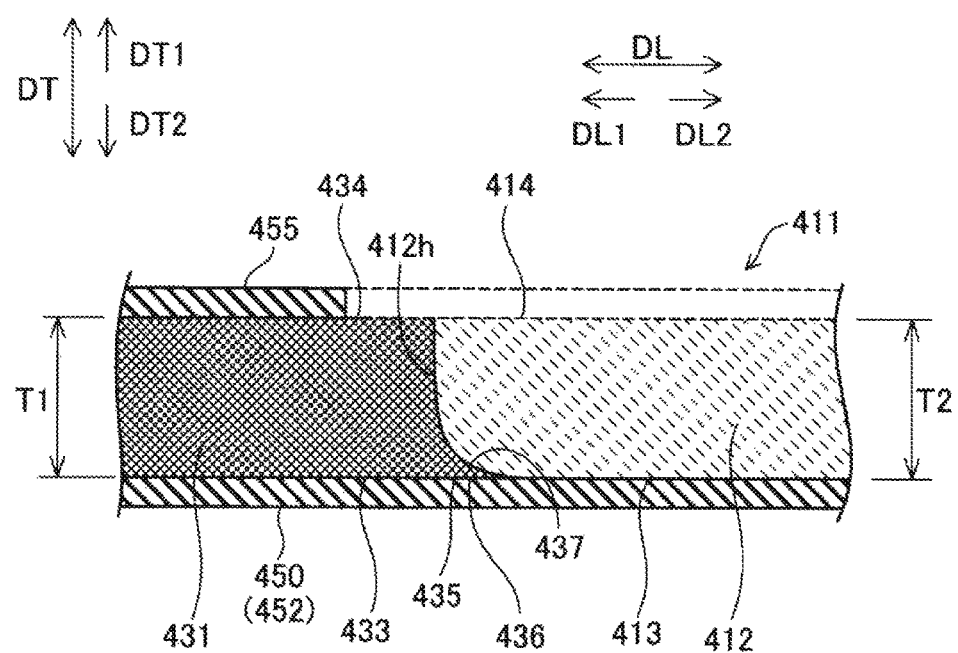
FIG. 10 is a view showing, on an enlarged scale, a cross-sectional portion AR2 shown in FIG. 9 and a vicinity thereof.

FIG. 10 is a view showing, on an enlarged scale, a cross-sectional portion AR2 shown in FIG. 9 and a region therearound. As shown in FIG. 10, the structure of the region around the boundary between the electrolyte portion 431 and insulating portion 412 of the composite ceramic layer 411 is similar to the structure in the first embodiment shown in FIG. 4. Specifically, the thickness T1 of the electrolyte portion 431 is substantially the same as the thickness T2 of the insulating portion 412. The first insulating surface 413 is flush with the first electrolyte surface 433. In a cross section of the composite ceramic layer 411 obtained by cutting the composite ceramic layer 411 in the thickness direction DT, the electrolyte portion 431 has, on the first electrolyte surface 433 side, an extension portion 435 extending outward from the through hole 412h so as to overlap the insulating portion 412 in the thickness direction DT. The thickness of the extension portion 435 decreases toward the outer circumference of the extension portion 435. The outer circumference of the extension portion 435 is continuously connected to the first insulating surface 413. A first extending surface 436 of the extension portion 435 that is a surface thereof on the other side DT2 is included in the first electrolyte surface 433 and continuously connects the first insulating surface 413 to the first electrolyte surface 433. Therefore, the first insulating surface 413, the first extending surface 436, and the first electrolyte surface 433 are connected to one another so as to form a single flat surface with no steps. A side wall portion 437 of the insulating portion 412 which defines the through hole 412h has an outwardly convex arcuate surface on the side where the first insulating surface 413 is present. Specifically, on the first insulating surface 413 side, the opening area of the through hole 412*h* increases from the inner side in the thickness direction toward the outer side. The structure shown in FIG. 10 is formed over the entire outer circumference of the electrolyte portion 431.

Also in the second embodiment described above, the occurrence of cracking or breakage of the first conductor layer 450 formed so as to extend continuously from the first insulating surface 413 to the first electrolyte surface 433 can be suppressed. In addition, the same effects as those in the first embodiment are obtained. In the second embodiment, the extension portion 435 is formed on the surface of the composite ceramic layer 411 that is located on the other side DT2. However, the extension portion 435 may be formed on the surface on the one side DT1. The extension portion 435 may be formed on each of the opposite surfaces of the composite ceramic layer 411 that are located on the one side DT1 and the other side DT2.

C. Modifications

<Modification 1>

In each of the embodiments described above, the extension portion is formed over the entire circumference of the electrolyte portion of each composite ceramic layer. However, the extension portion may be formed only in a portion of the outer circumference of the electrolyte portion which portion is in contact with the conductor layer. Even with this configuration, the occurrence of cracking or breakage of the conductor layer can be suppressed.

<Modification 2>

In each of the embodiments described above, the side wall portion of the insulating portion that defines the through hole has an arcuate surface on the side where the first insulating surface is present. However, the side wall portion may have an inclined surface.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2015-092548 filed Apr. 30, 2015, incorporated herein by reference in its entirety.

What is claimed is:

1. A gas sensor element comprising:
a composite ceramic layer including a plate-shaped insulating portion that contains an insulating ceramic and has a through hole passing through the insulating portion in a thickness direction thereof and a plate-shaped electrolyte portion that contains a solid electrolyte ceramic and is disposed in the through hole; and
a first conductor layer extending continuously from a first insulating surface on one side of the insulating portion to a first electrolyte surface of the electrolyte portion facing the same direction as the one side of the insulating portion, wherein
the first insulating surface is flush with the first electrolyte surface,
the electrolyte portion has an extension portion located on the side where the first electrolyte surface is present and extending outward from the through hole so as to overlap the insulating portion, and
the thickness of the extension portion decreases toward an outer circumference of the extension portion,
wherein a side wall portion of the insulating portion which defines the through hole and which separates the insulating portion from the electrolyte portion has an outwardly convex arcuate surface continuously extending into the electrolyte portion across an entire thickness thereof.

2. A gas sensor comprising the gas sensor element as claimed in claim 1.

3. A method of manufacturing the gas sensor element as claimed in claim 1,
the method comprising the steps of:
(A) inserting a green electrolyte portion into a through hole of a plate-shaped green insulating portion containing the insulating ceramic, the through hole extending through the green insulating portion in a thickness direction thereof, the green electrolyte portion containing the solid electrolyte ceramic and being thicker than the green insulating portion;
(B) compressing the green insulating portion and the green electrolyte portion simultaneously in the thickness direction such that a green first insulating surface of the green insulating portion on the one side is flush with a green first electrolyte surface of the green electrolyte portion facing the same direction as the one side;
(C) forming a green first conductor layer that extends continuously from the green first insulating surface to the green first electrolyte surface; and
(D) firing the green insulating portion, the green electrolyte portion, and the green first conductor layer to form the composite ceramic layer including the insulating portion and the electrolyte portion and to form the first conductor layer,
wherein, in step (A), a side wall portion of the green insulating portion that defines the through hole is chamfered on the side where the green first insulating surface is present, and
in step (B), a green extension portion that extends outward from the through hole so as to overlap the green insulating portion is formed on the side where the green first electrolyte surface of the green electrolyte portion is present such that the thickness of the green extension portion decreases toward an outer circumference of the green extension portion.

* * * * *